United States Patent [19]
Anderson

[11] Patent Number: 5,904,148
[45] Date of Patent: May 18, 1999

[54] DELAYED RELEASE FLAVORANT COMPOSITIONS

[75] Inventor: Denise Anderson, Zurich, Switzerland

[73] Assignee: Givaduan-Roure (International) SA, Vernier-Geneve, Switzerland

[21] Appl. No.: 08/657,864

[22] Filed: May 31, 1996

[30] Foreign Application Priority Data

Jun. 8, 1995 [EP] European Pat. Off. ............. 95810375

[51] Int. Cl.⁶ .............................. A24B 3/12; A24B 15/20; A24B 15/30
[52] U.S. Cl. ............................ 131/276; 131/274; 512/1; 512/8; 512/20
[58] Field of Search ................................. 131/276, 274, 131/310, 352, 275; 512/1, 8, 20; 585/610

[56] References Cited

U.S. PATENT DOCUMENTS

| | | | |
|---|---|---|---|
| 3,762,423 | 10/1973 | Simpson et al. | 131/276 |
| 3,854,485 | 12/1974 | Mold et al. | 131/276 |
| 4,509,537 | 4/1985 | Houminer et al. | 131/276 |
| 4,538,627 | 9/1985 | Chan et al. | 131/276 |
| 4,638,816 | 1/1987 | Cox et al. | 131/276 |
| 4,690,157 | 9/1987 | Podraza | 131/276 |
| 5,172,705 | 12/1992 | Chan | 131/276 |
| 5,199,450 | 4/1993 | Houminer et al. | 131/276 |
| 5,228,461 | 7/1993 | Chan et al. | 131/276 |
| 5,301,693 | 4/1994 | Chan et al. | 131/276 |
| 5,320,131 | 6/1994 | Dull . | |
| 5,371,069 | 12/1994 | Christenson et al. | 512/12 |
| 5,538,018 | 7/1996 | Chan et al. | 131/276 |
| 5,747,443 | 5/1998 | Wahl et al. | 510/515 |
| 5,759,990 | 6/1998 | Wahl et al. | 510/515 |

FOREIGN PATENT DOCUMENTS

0578421A1  1/1994  European Pat. Off. .

OTHER PUBLICATIONS

Barry M. Trost, ed., "Comprehensive Organic Synthesis," vol. 3, 1991, pp. 563–611.
Patent Abstracts of Japan vol. 013, No. 388 (C–630), Aug. 28, 1989 & JP 01 135867 A (Adeka Argus Chem Co Ltd).

*Primary Examiner*—Robert H. Harrison
*Attorney, Agent, or Firm*—George W. Johnston; Robert A. Silverman; Mark E. Waddell

[57] ABSTRACT

Delayed release flavorant compositions containing flavor-release additives, namely 1,2-diols of the formula

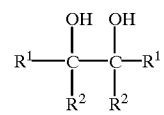

I wherein $R^1$ is one of the radicals

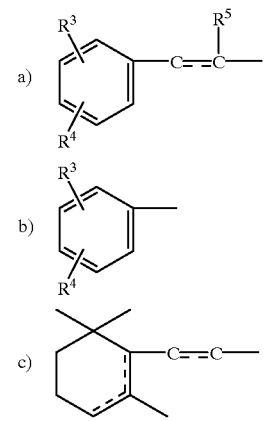

where $R^2$ is H, lower alkyl $R^3$, $R^4$ are H, lower alkyl, lower alkoxy, hydroxy, or $R^3+R^4$ together are methylenedioxy, $R^5$ is lower alkyl and the broken lines represent in the ring one additional bond and in the side chain an optional bond.

9 Claims, No Drawings

DELAYED RELEASE FLAVORANT COMPOSITIONS

FIELD OF THE INVENTION

The invention concerns delayed release flavorant compositions containing 1,2-diols as flavor-release additives.

SUMMARY OF THE INVENTION

The compositions of the invention are selected from the group consisting of
a) smoking compositions, e.g. tobacco, and
b) foodstuffs, in particular
   b1) bakeable foodstuffs and
   b2) microwaveable foodstuffs
containing flavor-release additives, namely 1,2-diols of the formula

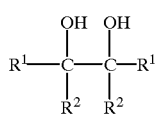
I wherein $R^1$ is one of the radicals

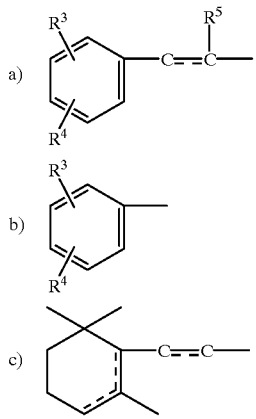

where
  $R^2$ is H, lower alkyl
  $R^3$, $R^4$ are H, lower alkyl, lower alkoxy, hydroxy, or $R^3$ and $R^4$ together are methylenedioxy,
  $R^5$ is lower alkyl
and the broken lines represent in the ring one additional bond
and in the side chain an optional bond.

DETAILED DESCRIPTION

The diols I possess no detectable flavor or odor themselves at normal temperatures and atmospheric conditions but function mainly as flavor precursors, in as far as they release a flavorant upon heating at higher temperatures, e.g. temperatures leading to pyrolysis and thermolysis, respectively. The diols I thus may be used as flavorants in smoking compositions, e.g. in tobacco compositions or tobacco substitutes, as sustained flavorants and odorants to mask or enhance the flavors and odors of burning tobacco products, and as flavor additives to foods, in particular bakeable and microwaveable foods.

The term lower alkyl and the alkyl portion of lower alkoxy radical suitably refers to straight or branched alkyl residues carrying from 1 to 6 carbon atoms. Suitable examples for the individual residues are as follows:
  $R^2$ H, $CH_3$, $C_2H_5$, etc.
  $R^3$, $R^4$ H, $CH_3$, $C_2H_5$, n- or iso- $C_3H_7$, t-$C_4H_9$, etc.
  $R^5$ $CH_3$, $C_2H_5$, n- or iso- $C_3H_7$, t-$C_4H_9$, $C_5H_{11}$, $C_6H_{13}$, etc.

Although the two radicals $R^1$ of formula I may be different 3 from each other and the two radicals $R^2$ may also be different from each other, in the preferred aspects these radicals $R^1$ and $R^2$ are the same.

As used herein the term "organoleptic" refers to compounds I which stimulate the sense of smell or taste, and are thus perceived as having a characteristic odor and/or flavor.

The terms "odor," "fragrance" and "smell" are used interchangeably whenever a compound is referred to as an organoleptic which is intended to stimulate the sense of smell.

The terms "flavor," "flavoring" and "flavorant" are also used interchangeably whenever an organoleptic compound is referred to which is intended to stimulate the sense of taste.

An "organoleptically effective amount" is a level or amount of the compounds(s) I present in a material at which the incorporated compound(s) exhibit(s) a sensory effect, e.g. by stimulating the sense of smell or taste.

The terms "tobacco" and "tobacco substitutes" are used in the conventional sense and include smokable as well as non-smokable forms in which tobacco is regularly used, e.g. cigarettes, snuff, chewable compositions, etc.

The term "tobacco paper" refers to smokable paper used to contain tobacco, e.g. tobacco rolling paper.

The terms "food" and "foodstuff" are used interchangeably.

The term "food product" would consequently designate the product of the process to which the foodstuff(s) containing the diol I is (are) subjected to.

The term "combustible filter" encompasses materials such as natural tobacco, reconstituted tobacco and tobacco substitutes, etc.

The term "tobacco substitute" is meant to include non-tobacco filled materials such as smoking products from sugar beet pulp, coffee bean hulls and other cellulosic or carbohydrate materials, etc.

The preferred compounds I are
  1,6-diphenyl-1,5-hexadiene-3,4-diol,
  2,5-dihexyl-1,6-diphenyl-1,5-hexadiene-3,4-diol and
  1,2-bis(4-hydroxy-3-methoxyphenyl)-1,2-ethanediol.
Further suitable compounds I include
  3,4-dimethyl-1,6-bis(2,6,6-trimethyl-1-cyclohexen-1-yl)-1,5-hexadiene-3,4-diol,
  3,4-dimethyl-1,6-bis(2,6,6-trimethyl-2-cyclohexen-1-yl)-1,5-hexadiene-3,4-diol,
  1,2-bis(1,3-benzodioxol-5-yl)-1,2-ethanediol,
  1,2-bis(4-methoxyphenyl)-1,2-ethanediol,
  1,2-diphenyl-1,2-ethanediol or
  1,6-bis(4-methoxyphenyl)-1,5-hexadiene-3,4-diol.

The compounds I possess organoleptic properties and therefore permit the development of methods useful in enhancing the flavor of foods. These compounds are also useful in enhancing the odor, masking any unpleasant odor or enhancing the flavor of tobacco products.

These compounds may be used individually in an amount effective to enhance a characteristic flavor or odor of a given material. The compounds may also be mixed with other flavor or fragrance components in an amount sufficient to provide the desired flavor or odor characteristic.

The amount required to produce the desired, overall effect varies depending upon the particular compound chosen, the product in which it will be used, and the particular effect desired.

For example, depending upon the selection and concentration of the compounds I used, addition of the compounds I, either singly or as a mixture, to cigarette tobacco at levels ranging from about 5 ppm to about 50,000 ppm tends to enhance the smoking flavor and/or mask undesirable smoking odors. An important property of these compounds I is that the flavorant or odorant is covalently bound as an non-volatile compound and it is only when the tobacco product is ignited and burns that the flavorant or odorant is released.

Addition of the diols I of formula I either separately or as a mixture at levels suitably ranging from about 5 ppm to about 50,000 ppm by weight onto the media enclosing the tobacco serves to incorporate the odorant/flavorant in the side-stream smoke as the tobacco product burns. Air borne flavorants and/or odorants along with other combustion products are thus introduced. This newly formed odorant or flavorant serves to enhance or mask the smoking odors depending upon selection and use levels of the compounds I.

The diols I are also particularly useful in the flavoring and aromatizing of cooked foods. Addition of the diols either singly or as a mixture to a cake batter, e.g. a microwave cake batter, serves to impart appropriate baking aromas to the cake as it is heated in the microwave as well as impart flavoring in the finished product. Typically, diols I are employed at levels ranging from about 0.0005 to about 10%, in particular from 0.05 to about 5.00%.

In addition to the baking aromas, other pleasant organoleptic properties may be provided, the palette is broad and may comprise— depending on the compound I used—floral, fruity, sweet, herbaceous, balsamic, spicy, cinnamon, woody, vanillin notes.

Notewortly are, furthermore, the stability of the novel flavorants.

A suitable temperature range may extend from about 70° C. to about 300° C., or even more.

The compounds I may be incorporated into the foodstuff or the smoking composition, e.g. the tobacco product along with other ingredients. Such other ingredients include emulsifiers, carriers, binders, sweeteners, stabilizers, buffers and solvents, etc.

The addition of the diol I may generally be effected according to methods known in the art, e.g. as such or dissolved in any suitable solvent, e.g. in an alcohol, such as ethanol or aqueous ethanol, etc. It may then be sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5–5 weight percent, based on the weight of filler, and then subsequently to blend the treated filler with filler which does not contain flavorant additive. Naturally, the additive can also be present as a surface coating or absorbed component of the paper wrapper, and/or the additive can be incorporated as a component of the adhesive formulation which is utilized to seal the sideseam of cigarette paper wrappers.

The flavorant additive is released preferably during ignition and burning of the smoking composition, e.g. the tobacco product or during the baking or the microwaving process of the foodstuff.

A large number of the compounds I—actually the majority thereof—are known. In as far as the novel compounds are concerned, the following applies:

Pinacol diols can be prepared from the corresponding aldehydes and ketones by standard methods known to those skilled in the art—see Comprehensive Organic Synthesis, Barry M. Trost, ed., Vol. 3, 1991, pp 563–579. For example, reaction of aldehydes or ketones with metals—e.g. Zn, Mg, Ce, Al(Hg) or Ti—and acid—e.g. acetic acid—provides pinacol diols I. Various aldehydes and ketones can also be transformed by electrochemical means to their pinacol diols. Pinacol diols can also be prepared by reduction of benzoins. All these methods are outlined by B. M. Trost.

Two compounds of this invention are novel, i.e. 1,6-bis(4-methoxyphenyl)-1,5-hexadiene-3,4-diol and 2,5-dihexyl-1,6-diphenyl-1,5-hexadiene-3,4-diol. These may be obtained by subjecting 1,4-methoxycinnamaldehyde or α-hexylcinnamaldehyde to pinacolisation as outlined above.

EXAMPLES

The following examples are set forth herein to illustrate methods of synthesis of the pinacol diol derivatives I and their use as flavorants and flavor precursors. These examples are intended only to illustrate the embodiments of this invention and are in no way meant to limit the scope thereof.

All parts, proportions, percentages and ratios used herein are by weight unless otherwise indicated.

Example 1

1,6-Diphenyl-1,5-hexadiene-3,4-diol

A mixture of cinnamaldehyde (200 g, 1.5 mol), zinc (98.9 g, 1.5 mol), water (380 ml), and ether (230 ml) was heated to reflux under a nitrogen atmosphere. Acetic acid (175 ml) was added over a 2 hour period. The reaction was heated at reflux for an additional 3 hours. The mixture was cooled and filtered. Ethyl acetate and ether (1:2) were added and the mixture was washed sequentially with water (2 x), aqueous sodium bicarbonate solution until neutral, brine, and dried over sodium sulfate, filtered, and the solvent was evaporated under reduced pressure. The syrup obtained was crystallized from ethyl acetate to give meso-1,6-diphenyl-1,5-hexadiene-3,4-diol.

mp: 150°–152° C., $^1$H-NMR (CDCl$_3$) d 7.42–7.20 (10H, m), 6.71 (2H, d, J=15.87 Hz), 6.29 (2H, dd, J=6.41 and 15.87 Hz), 4.49–4.39 (2H, m), 2.24 (2H, OH). IR (KBr) 3298, 2908, 1449, 963, 746 cm$^{-1}$. MS m/e (% abundance) 266 (1), 133 (100), 115 (22), 77 (25), 55 (67).

d,l-1,6-Diphenyl-1,5-hexadiene-3,4-diol can be isolated from the reaction mixture.

$^1$H-NMR (CDCl$_3$) d 7.42–7.20 (10H, m), 6.72 (2H, d, J=16.17 Hz), 6.34–6.18 (2H, m), 4.32–4.24 (2H, m), 2.55 (2H, s). IR (KBr) 3313, 1449, 1047, 970, 690 cm$^{-1}$. MS m/e (% abundance) 266 (1), 133 (100), 115 (25), 55 (29).

Example 2

1,6-Bis(4-methoxyphenyl)-1,5-hexadiene-3,4-diol

In a fashion similar to that described in Example 1, 1,4-methoxycinnamaldehyde was treated with zinc and acetic acid to provide 1,6-bis(4-methoxyphenyl)-1,5-hexadiene-3,4-diol.

mp: 145°–146° C. $^1$H-NMR (CDCl$_3$) d7.34–7.28 (4H, m), 6.86–6.61 (4H, m), 6.69–6.59 (2H, m), 6.29–6.06 (2H, m), 3.80 (6H, s). IR (KBr) 3365, 2956, 2838, 1606, 1512, 1252, 1031 cm$^{-1}$. MS m/e (% abundance) 326 (1), 163 (100), 55 (18).

Example 3
2,5-Dihexyl-1,6-diphenyl-1,5-hexadiene-3,4-diol

In a fashion similar to that described in Example 1, α-hexyl-cinnamaidehyde was treated with zinc and acetic acid to provide 2,5-dihexyl-1,6-diphenyl-1,5-hexadiene-3,4-diol.

mp: 86–86.5, $^1$H-NMR (CDCl$_3$) d 7.38–7.16 (10H, m), 6.73 (2H, bs), 4.33 (2H, bs), 2.56–2.46 (4H, m), 2.14–2.06 (2H, m), 1.60–1.49 (4H, m), 1.40–1.21 (10H, m), 0.90–0.84 (6H, m). IR (KBr) 3455, 3296, 2922, 2853, 1454, 1091, 699 cm$^{-1}$. MS m/e (% abundance) 434 (3), 218 (46), 217 (100), 91 (22).

Example 4
Preparation of an α-hexylcinnamaldehyde cigarette

An ethyl acetate solution of the compound from Example 3 was applied to cigarette papers at the rate of 1000 ppm. (Application rates of 5 to 50,000 ppm may actually be useful). The paper was incorporated into cigarettes. Prior to smoking, no odor of α-hexylcinnamaldehyde was observed. Upon smoking, a noticeable and persistent floral odor was observed in the room air. The floral odor was, actually, already observed on first puff.

Example 5
Preparation of a vanillin cigarette

An alcohol/water solution of the compound 1,2-bis(4-hydroxy-3-methoxyphenyl)-1,2-ethanediol was applied to cigarette papers at the rate of 500 ppm. The paper was incorporated into cigarettes. Prior to smoking, no odor of vanillin was observed. Upon smoking a faint, but distinct odor of vanillin was observed in the room air.

I claim:

1. A smoking composition comprising the flavorant-release additive being a 1,2 diol of the formula

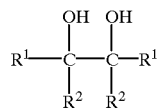

I wherein R$^1$ is one of the radicals

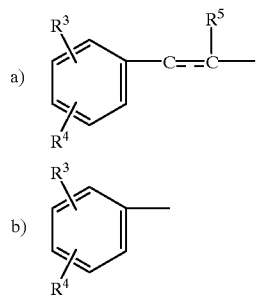

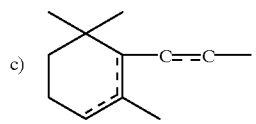

where

R$^2$ is H, lower alkyl

R$^3$, R$^4$ are H, lower alkyl, lower alkoxy, hydroxy, or R$^3$+R$^4$ together are methylenedioxy, R$^5$ is lower alkyl and the broken lines represent in the ring one additional bond and in the side chain an optional bond.

2. The composition according to claim 1, wherein the concentration of the flavorant-release additive is about 0.0005 to about 10% w/w.

3. The composition according to claim 1, wherein R$^3$ and R$^4$ in the formula I a) diol is hydrogen.

4. The composition according to claim 1, wherein R$^2$ is hydrogen.

5. The composition according to claim 1, wherein R$^2$ in the formula I b) diol is methyl.

6. The composition according to claim 1, wherein R$^2$ in the formula I c) diol is methyl and there is an optional bond in the side chain of the molecule.

7. The composition according to claim 1, wherein the compound of Formula I is 1,6-diphenyl-1,5-hexadiene-3,4-diol, 3,4-dimethyl-1,6-bis(2,6,6-trimethyl-1-cyclohexen-1-yl)-1,5-hexadiene-3,4-diol, 3,4-dimethyl-1,6-bis(2,6,6-trimethyl-2-cyclohexen-1-yl)-1,5-hexadiene-3,4-diol, 1,2-bis(4-hydroxy-3-methoxyphenyl)-1,2-ethanediol, 1,2-bis(1,3-benzodioxol-5-yl)-1,2-ethanediol, 1,2-bis(4-methoxyphenyl)-1,2-ethanediol, 1,2-diphenyl-1,2-ethanediol, 1,6-bis(4-methoxyphenyl)-1,5-hexadiene-3,4-diol or 2,5-dihexyl-1,6-diphenyl-1,5-hexadiene-3,4-diol.

8. A composition according to claim 1 wherein the composition is a cigarette.

9. The composition according to claim 2, wherein the concentration of the flavorant-release additive is about 0.005 to about 5% w/w.

* * * * *